United States Patent [19]
Wasserman

[11] Patent Number: 5,862,973
[45] Date of Patent: Jan. 26, 1999

[54] METHOD FOR INSPECTING SOLDER PASTE IN PRINTED CIRCUIT BOARD MANUFACTURE

[75] Inventor: Harold Wasserman, Skillman, N.J.

[73] Assignee: Teradyne, Inc., Boston, Mass.

[21] Appl. No.: 791,390

[22] Filed: Jan. 30, 1997

[51] Int. Cl.[6] .................................................. B23K 31/12
[52] U.S. Cl. ........................................... 228/105; 228/103
[58] Field of Search .................................... 228/103, 105, 228/56.5

[56] References Cited

U.S. PATENT DOCUMENTS

| | | | |
|---|---|---|---|
| 4,688,939 | 8/1987 | Ray | 356/237 |
| 4,941,256 | 7/1990 | Capson et al. | 228/103 |
| 4,978,220 | 12/1990 | Abramovich et al. | 356/394 |
| 5,060,065 | 10/1991 | Wasserman | 358/106 |
| 5,245,421 | 9/1993 | Robertson et al. | 358/101 |
| 5,260,779 | 11/1993 | Wasserman | 358/93 |
| 5,517,235 | 5/1996 | Wasserman | 348/126 |
| 5,621,811 | 4/1997 | Roder et al. | 382/147 |

FOREIGN PATENT DOCUMENTS

| | | | |
|---|---|---|---|
| 61-293657 | 12/1986 | Japan | 228/103 |
| 3-215704 | 9/1991 | Japan | 228/103 |
| 4-76443 | 3/1992 | Japan | 228/105 |

OTHER PUBLICATIONS

A.S. Cammarano and J.J. Hinderer, "Optical Testing of Solder Pads," *IBM Tech. Discl. Bull.*, vol. 21, No. 7, Dec. 1978, pp. 2914–2915.

T. Ross and A. Townsend, "Inspection Technique for Solder Reflow Pad Height/Volume," *IBM Tech. Discl. Bull.*, vol. 22, No. 9, Feb. 1980, p. 4068.

"Solder Joint Inspection System Using Fuzzy Theory," *IBM Tech. Discl. Bull.*, vol. 33, No. 10A, Mar. 1991, p. 324.

"Algorithm to Detect Solder Bridge on Printed Circuit Board," *IBM Tech. Discl. Bull.*, vol. 33, No. 10A, Mar. 1991, pp. 417–418.

*Primary Examiner*—Patrick Ryan
*Assistant Examiner*—Jeffrey T. Knapp
*Attorney, Agent, or Firm*—Richard E. Gamache

[57] ABSTRACT

A method is available for inspecting a printed circuit board and solder paste deposited upon the printed circuit board, whereby both systematic defects occurring during a solder paste deposition process and random defects are located. The printed circuit board is continuously scanned by an inspection head immediately following the solder paste deposition process. Images of the printed circuit board are then analyzed for random defects such as missing solder paste, improper solder paste coverage, and solder bridging. Next, heights of solder paste deposits are sampled. A pattern of light is projected upon selected solder paste deposits, and images of the selected solder paste deposits are captured. Light triangulation techniques are then used for determining the height of each selected solder paste deposit. Variations in the height of solder paste are systematic defects occurring in the solder paste deposition process.

14 Claims, 4 Drawing Sheets

METHOD FOR INSPECTING SOLDER PASTE IN PRINTED CIRCUIT BOARD MANUFACTURE

This invention relates generally to the manufacture of printed circuit boards, and more specifically, to manufacturing defect analyzers.

Printed circuit boards are typically tested during the manufacturing process for determining whether the circuit boards contain manufacturing defects. In this way, defective printed circuit boards can be identified before being incorporated into electronic products, thereby minimizing the chance that the electronic products will fail prematurely in the field.

Electronic components designed using "surface mount" technology, also known as surface mount components, are commonly found on today's densely populated printed circuit boards. Whereas electronic components designed using traditional "through-hole" techniques typically have leads that are inserted though metalized holes on printed circuit boards, surface mount components generally have leads or conductive pads that are adapted for making contact with corresponding conductive pads on surfaces of the printed circuit boards.

The following processes are generally performed by printed circuit board manufacturers for mounting and interconnecting surface mount components to a printed circuit board: solder paste deposition, component placement, and reflow.

The solder paste deposition process typically includes depositing solder paste on conductive pads located on a surface of the printed circuit board. Also, the component placement process typically includes placing surface mount components on the surface of the printed circuit board such that the leads or pads of each surface mount component align with corresponding conductive pads on the printed circuit board surface. The solder paste deposited during the solder paste deposition process generally keeps the surface mount components in place following the component placement process.

Finally, the reflow process typically includes adding heat to the printed circuit board assembly, thereby causing the solder paste to soften. When the heat is removed, the solder solidifies and forms both a mechanical and an electrical connection between the leads or pads of each surface mount component and the corresponding conductive pads on the surface of the printed circuit board.

However, manufacturing defects can occur while mounting and interconnecting surface mount components to printed circuit boards. In particular, solder paste might not adhere to a respective conductive pad on the printed circuit board surface following the solder paste deposition process. This could result in an electrical open circuit between the conductive pad and its corresponding lead or pad on a surface mount component following the component placement and reflow processes.

Even if the deposited solder paste adheres properly to the respective conductive pad on the circuit board, either too much or too little solder paste might be present. If too much solder paste were deposited, then the conductive pad on the circuit board could make electrical connection with more than one pad on a surface mount component following the reflow process. Alternatively, if too little solder paste were deposited, then a poor mechanical and electrical connection might result between the conductive pad and its corresponding lead or pad on the surface mount component. Also, solder paste on adjacent conductive pads on the circuit board could merge together, thereby forming an electrical short circuit or "bridge", between the adjacent conductive pads.

One method of locating manufacturing defects on printed circuit boards uses a technology known as automated optical inspection (AOI). A manufacturing defect analyzer designed using AOI techniques is disclosed in U.S. Pat. No. 5,245,421 entitled "Apparatus for Inspecting Printed Circuit Boards with Surface Mount Components," and assigned to Control Automation Incorporated, Princeton, N.J. This defect analyzer, which includes video cameras having respective light sources mounted in a movable inspection head, can accurately verify the presence and orientation of a particular surface mount component, and can also reliably check the quality of the solder connecting the surface mount component to the circuit board.

Nevertheless, the defect analyzer described above has been found to be inappropriate for inspecting some high density printed circuit board designs. This is because the solder connecting surface mount components to the circuit board is sometimes hidden after the component placement and reflow processes. As a result, the defect analyzer described above cannot always reliably check the quality of the solder connections.

This is generally the case for newer chip carrier designs such as ball grid array (BGA) devices, which use solder paste in a matrix array for connecting tiny leads to respective conductive pads on printed circuit boards. Like some surface mount components, solder connecting BGA devices to printed circuit boards cannot be easily seen. Consequently, the solder connections cannot be reliably checked using traditional AOI methods.

Another method of locating manufacturing defects on printed circuit boards uses x-ray technology. A manufacturing defect analyzer designed using x-ray technology can be used for checking the quality of hidden solder. For this reason, x-ray inspection is suitable for inspecting solder connecting BGA devices to printed circuit boards.

However, x-ray inspection also has some drawbacks. In particular, checking solder connections using x-ray inspection sometimes results in "false rejects," which are indications of faulty solder connections when the inspected solder connections are actually good. For example, an x-ray image of insufficiently reflowed solder might be virtually identical to a corresponding x-ray image of properly reflowed solder. Also, x-ray images of printed circuit boards having components mounted to both sides of the boards sometimes have solder connections on one side superimposed over solder connections on another side, thereby making accurate evaluation of the solder connections almost impossible.

Further, false rejects of solder connecting BGA devices to a printed circuit board typically lead to removal of the BGA devices from the circuit board, thereby possibly destroying the BGA devices and damaging the printed circuit board. Also, virtually all x-ray inspection systems currently in use occasionally yield false rejects.

Because the use of chip carrier designs such as BGA devices has increased, it would be desirable to have a manufacturing defect analyzer with testing capabilities that extend beyond traditional AOI and x-ray inspection systems. Such a defect analyzer would be able to inspect solder paste on a printed circuit board, and operate fast enough for use in typical printed circuit board assembly lines.

SUMMARY OF THE INVENTION

With the foregoing background in mind, it is an object of the invention to provide a reliable way of detecting faulty solder paste for connecting electronic components to printed circuit boards.

Another object of the invention is to provide a way of detecting missing solder paste and improper solder paste coverage on conductive pads on a printed circuit board surface, and solder paste bridging between closely-spaced conductive pads.

Still another object of the invention is to provide a manufacturing defect analyzer for detecting faulty solder paste on conductive pads on a printed circuit board surface that is compatible with typical assembly line rates.

The foregoing and other objects are achieved by providing a manufacturing defect analyzer for inspecting a printed circuit board immediately following a solder paste deposition process. The manufacturing defect analyzer takes a two-pronged approach for inspecting the printed circuit board. First, the manufacturing defect analyzer obtains an indication of whether the solder paste deposition process is "in-control," in accordance with statistical process control techniques, by sampling heights of solder paste deposited upon selected conductive pads on a printed circuit board surface. Second, the manufacturing defect analyzer inspects solder paste deposited upon each conductive pad on the printed circuit board surface for proper coverage, and then inspects each pair of adjacent conductive pads for solder bridges improperly connecting the adjacent conductive pads.

One feature of the manufacturing defect analyzer includes an improved lighting system for measuring the heights of solder paste deposited upon selected conductive pads. In the preferred embodiment, the improved lighting system incorporates a projector for projecting a "cross" pattern of light on the solder paste deposited on the selected conductive pads.

Still further objects and advantages will become apparent from a consideration of the ensuing description and drawings.

BRIEF DESCRIPTION OF THE DRAWINGS

The invention will be better understood by reference to the following more detailed description and accompanying drawings in which.

DESCRIPTION OF THE PREFERRED EMBODIMENT

Figure 1:
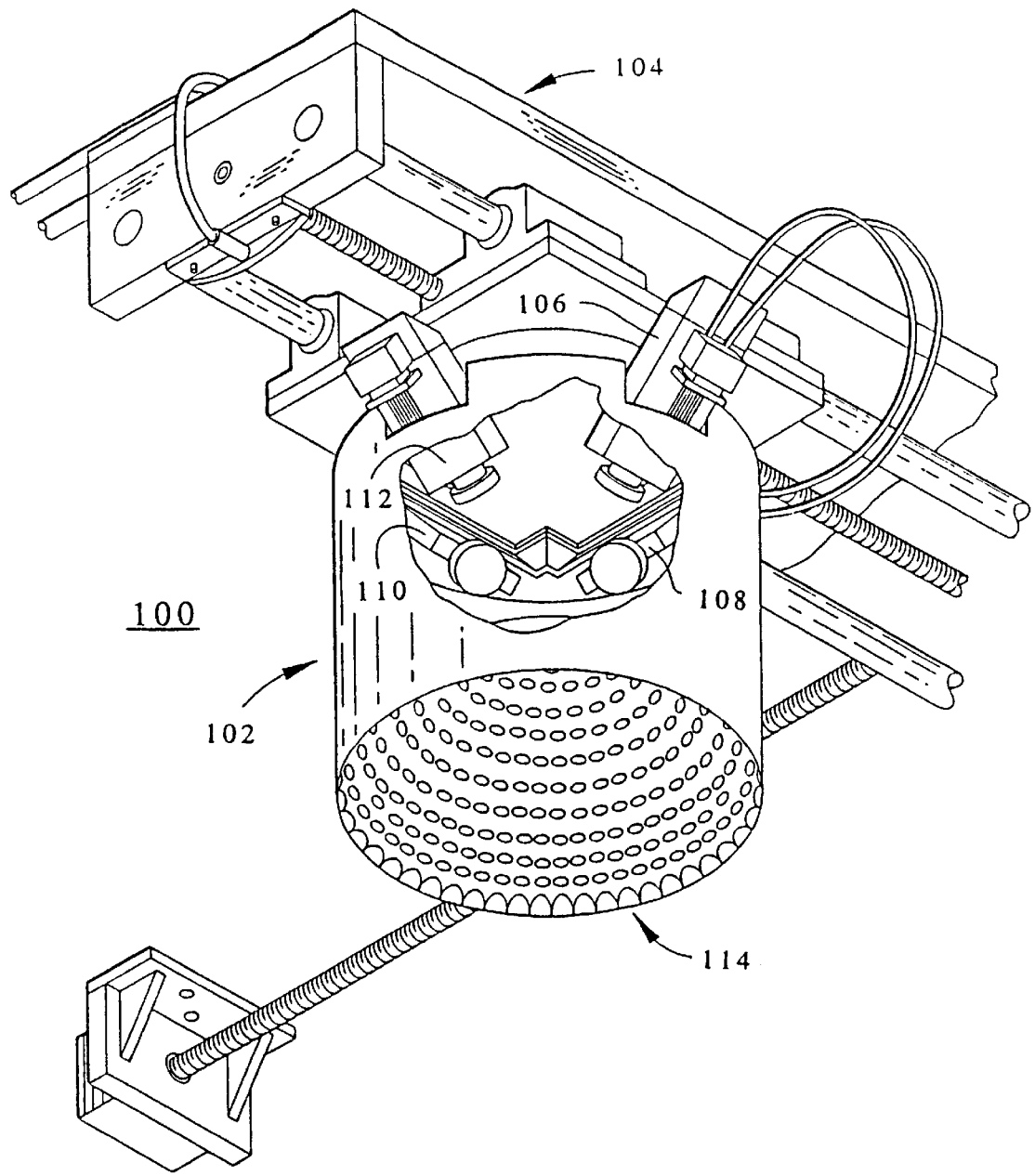
FIG. 1 is an isometric view of the inspection head of a prior art manufacturing defect analyzer for printed circuit boards.

FIG. 1 shows prior art manufacturing defect analyzer 100, which includes several features that are also part of the present invention.

In particular, defect analyzer 100 includes inspection head 102, which is supported and moved in a defined plane by X-Y table 104 (partially shown). Inspection head 102 includes video cameras 106, 108, 110, and 112. Inspection head 102 also includes lighting fixture 114 for selectively illuminating a printed circuit board under inspection so that appropriate images can be captured by video cameras 106, 108, 110, and 112.

It should be understood that inspection head 102, X-Y table 104, video cameras 106, 108, 110, and 112, and lighting fixture 114 generally correspond to known components. For example, additional detail about the general construction and operation of inspection head 102, X-Y table 104, and video cameras 106, 108, 110, and 112 can be obtained by referring to U.S. Pat. No. 5,245,421 assigned to Control Automation Incorporated, Princeton, N.J., which is incorporated herein by reference.

Further, additional detail about lighting fixture 114 can be obtained by referring to U.S. Pat. No. 5,060,065 assigned to Cimflex Teknowledge Corporation, Princeton, N.J., which is also incorporated herein by reference. For this reason, discussion of the present invention will proceed with descriptions of an improved way of illuminating the printed circuit board under inspection, and a new way of using the known components listed above for inspecting the printed circuit board during the manufacturing process.

Figure 2:
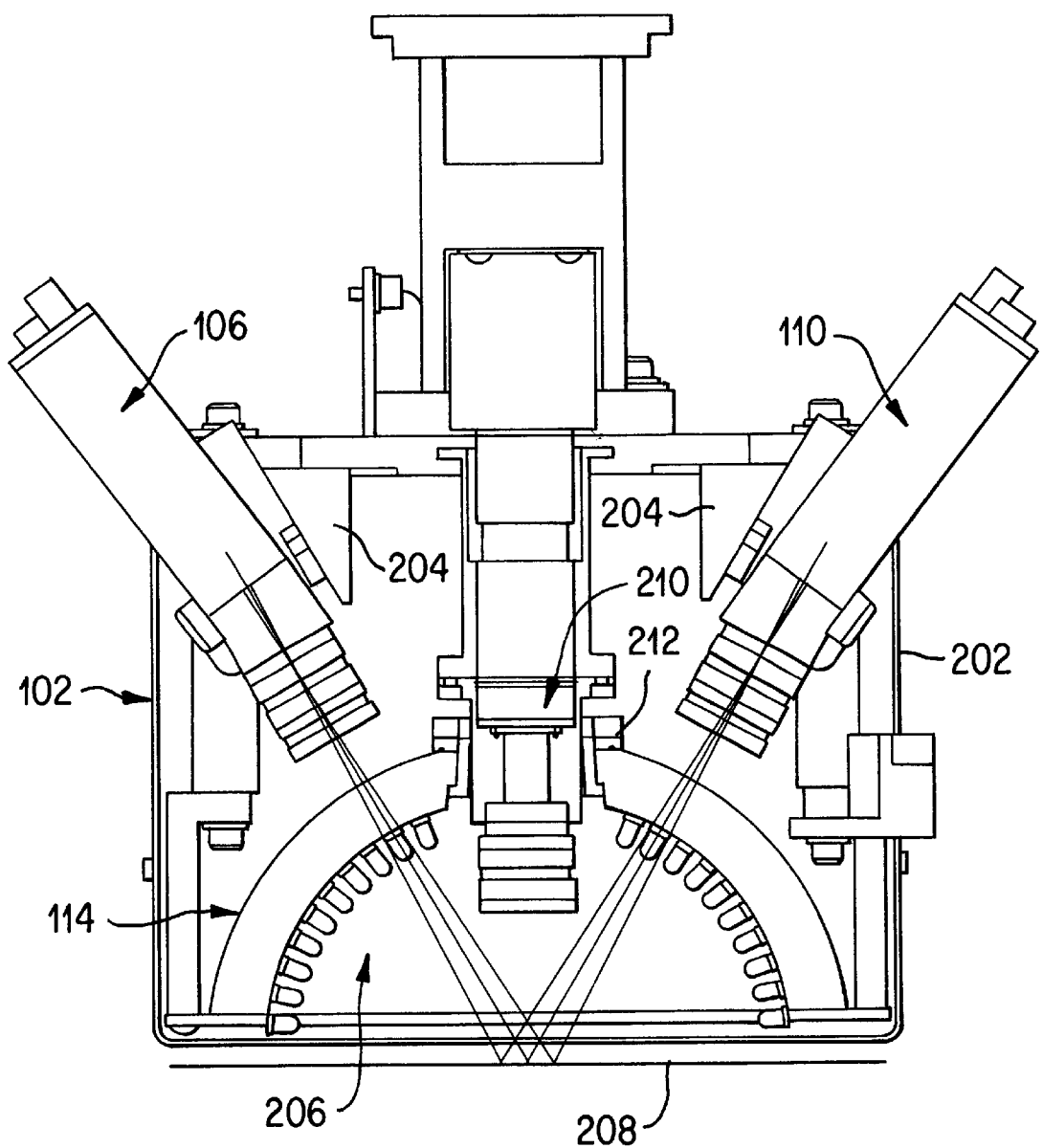
FIG. 2 is a cross-sectional view of the inspection head according to the present invention.

FIG. 2 shows a cross-sectional view of inspection head 102 for describing some components in greater detail. In particular, video cameras 106 and 110 are secured to enclosure 202 by mountings 204. Also, video camera 112 is located behind projector 210, and video camera 108 is situated as shown in FIG. 1.

Lighting fixture 114 is mounted to open end 206 such that lighting fixture 114 is in registration with printed circuit board 208. Also, apertures (not shown) are provided in lighting fixture 114 so that video cameras 106, 108, 110, and 112 can capture images of printed circuit board 208. Video cameras 106, 108, 110, and 112 are preferably positioned so that their respective axes converge at the base of enclosure 202, thereby defining a viewing field on printed circuit board 208.

As mentioned above, inspection head 102 includes projector 210, which extends through aperture 212 at the base of lighting fixture 114. Projector 210 is preferably disposed in inspection head 102 in an axial, centrally located position. Further, projector 210 preferably projects coherent light in a "cross" pattern upon solder paste deposited on selected conductive pads on a surface of printed circuit board 208. In the preferred embodiment, projector 210 includes a xenon flash tube (not shown) for illuminating the solder paste and a reticle (not shown) for forming the cross pattern on the solder paste.

Inspection head 102 preferably inspects solder paste on printed circuit board 208 immediately following a solder paste deposition process, before electronic components are placed on printed circuit board 208. This is because solder connecting the electronic components to printed circuit board 208 may be hidden between the components and printed circuit board 208, thereby making inspection of the solder connections virtually impossible using traditional circuit board inspecting methods. BGA devices, which are increasingly found on densely populated printed circuit boards, are examples of electronic devices with hidden solder connections.

During a typical solder paste deposition process, each conductive pad on printed circuit board 208 that is designed for making electrical contact with a lead or pad of an electronic component has solder paste deposited upon it. Because the solder paste deposited upon each conductive pad is generally shaped like a brick, it is commonly called a "solder brick."

Inspection head 102 preferably inspects solder bricks for both improper height and improper coverage of a respective conductive pad on the surface of printed circuit board 208. Also, inspection head 102 preferably inspects the surface of printed circuit board 208 for solder bridges, which might connect closely-spaced conductive pads on the surface of printed circuit board 208.

It has been found that the heights of solder bricks deposited on a printed circuit board during the solder paste deposition process deviate from the norm rather infrequently. For this reason, inspection head 102 usually does not inspect the height of every solder brick deposited on printed circuit board 208. In the preferred embodiment, known statistical process control (SPC) methods are used for analyzing the heights of the solder bricks, and for determining an appropriate rate at which to sample the solder brick heights. If the SPC methods show that the solder paste deposition process is approaching an "out-of-control" condition, then an operator can temporarily halt the process and perform necessary adjustments before systematic defects appear on the printed circuit board. For example, height variations of solder bricks might be caused by incorrect squeegee pressure or by incorrect solder paste temperature.

Figure 3:
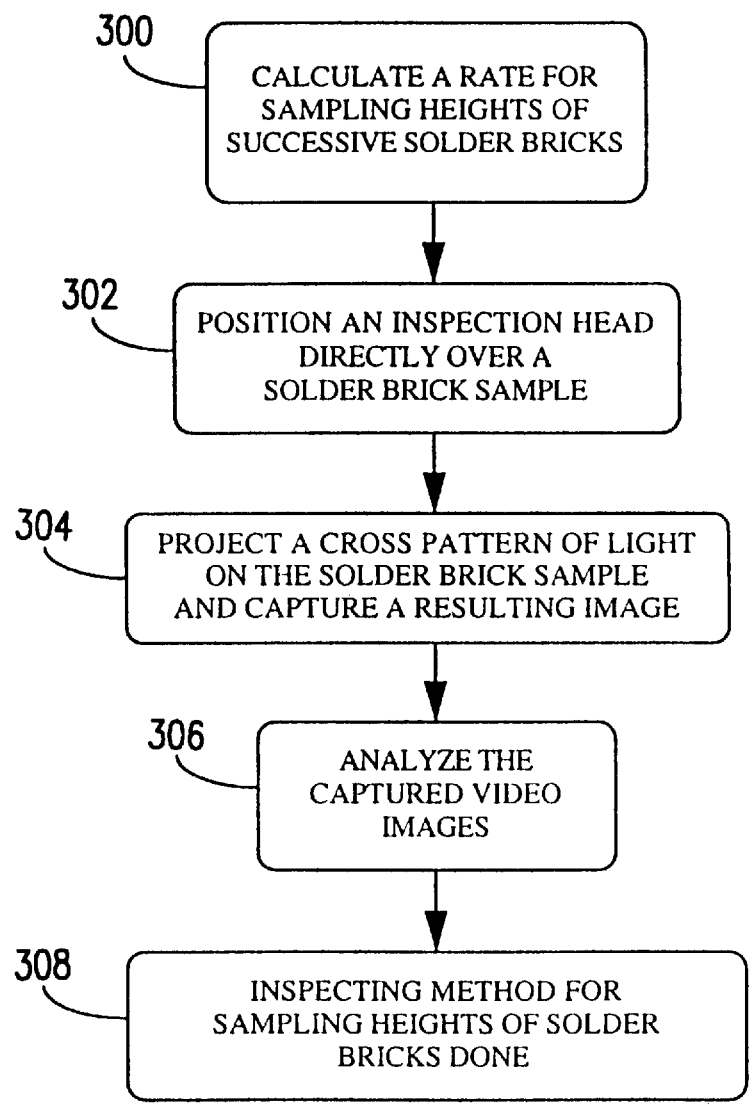
FIG. 3 is a flowchart depicting an inspecting method according to the present invention.

According to the procedure shown in FIG. 3, solder bricks are inspected for improper height as follows. First, an appropriate rate is calculated in block 300 for sampling heights of successive solder bricks. Inspection head 102, including projector 210 and video cameras 106, 108, 110, and 112, is then positioned directly over a solder brick sample (not shown) on printed circuit board 208 in block 302.

Next, projector 210 is activated in block 304, thereby momentarily projecting the cross pattern of light downwardly toward the solder brick sample. The cross pattern preferably falls onto a top surface of the solder brick, and then continues down each side until it just strikes the surface of printed circuit board 208. Also, at least one of video cameras 106, 108, 110, and 112 is activated synchronously with projector 210 in block 304, thereby capturing an image of the solder brick sample while the cross pattern persists on its surface.

The image captured by the video camera is then analyzed in block 306 for inspecting the height of the solder brick. In the preferred embodiment, known light triangulation techniques are used. For example, triangulation techniques can be used for measuring a distance between the ends of the line of light falling down at least one side of the solder brick. The measured distance is proportional to the solder brick height. The procedure outlined above can be used for accurately measuring the height of a solder brick to within 0.25 mil.

It has also been found that defects which might be caused by clogged stencils, air bubbles, etc., occur somewhat randomly during the solder paste deposition process. Clogged stencils might cause missing solder paste, whereas air bubbles might cause voids in solder bricks. For this reason, inspection head 102 preferably inspects every solder brick deposited on printed circuit board 208 for random defects.

Figure 4:
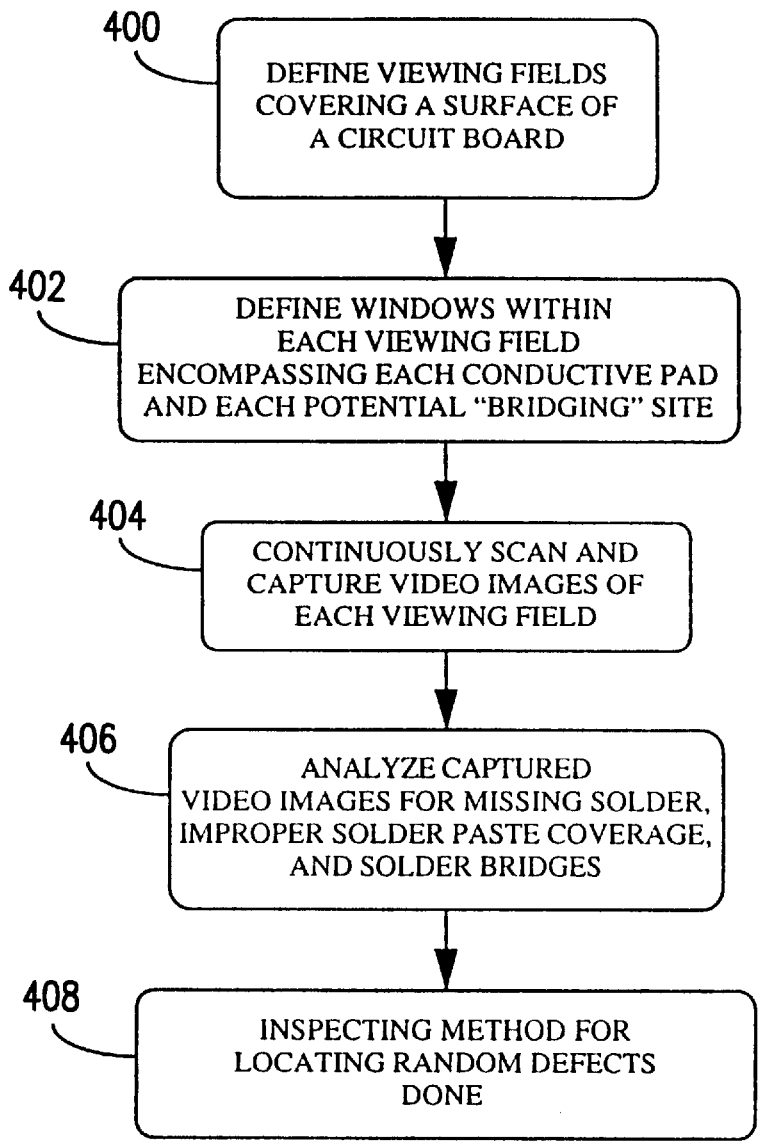
FIG. 4 is a flowchart depicting another inspecting method according to the present invention.

According to the procedure shown in FIG. 4, solder bricks are inspected for random defects as follows. First, a plurality of viewing fields is defined in block 400 as described above, such that each solder brick deposited on printed circuit board 208 is located within one of the viewing fields.

The dimensions of each viewing field are preferably 1 inch by 1 inch. With these dimensions, inspection head 102 typically scans printed circuit board 208 at a rate of 1 inch/33 msec, or about 30 inches per second. This results in a scanning rate of about 30 square inches per second, assuming a scan width of 1 inch. Further, each viewing field abuts adjacent viewing fields without overlapping.

Next, a plurality of windows are defined within each viewing field to be inspected in block 402. The windows correspond to the locations of the solder bricks on printed circuit board 208, and to areas on the surface of printed circuit board 208 where solder bridges might form.

Inspection head 102 then continuously and successively scans the viewing fields in block 404. While X-Y table 104 positions inspection head 102 above one of the windows, selected LEDs in lighting fixture 114 are momentarily activated and images are captured by selected video cameras in accordance with the details disclosed in U.S. Pat. No. 5,060,065.

The images captured by the video cameras are then analyzed in block 406 for inspecting printed circuit board 208 for random defects. In the preferred embodiment, printed circuit board 208 is inspected for missing solder paste by analyzing contrasts between levels of reflected light within an appropriate window. For example, solder bricks are typically very specular and therefore easily reflect the light produced by the selected LEDs back toward the selected video cameras. A substantial amount of the reflected light results from a "corner effect" as disclosed in U.S. Pat. No. 5,245,421.

The conductive pads on printed circuit board 208 upon which the solder bricks are deposited also tend to be specular. This is because the conductive pads are typically wetted with solder paste during the solder paste deposition process. However, the conductive pads are substantially planar and therefore cannot take advantage of the corner effect for reflecting light toward the selected video cameras. As a result, if the amount of reflected light detected by the selected video cameras meets or exceeds a prescribed threshold, then the solder brick is situated upon its respective conductive pad on printed circuit board 208. Otherwise, if the amount of detected light is below the prescribed threshold, then the solder brick is missing.

Printed circuit board 208 is also preferably inspected for improper solder paste coverage. Once again, this inspection method takes advantage of a solder brick's ability to reflect light toward selected video cameras. Accordingly, the images of an appropriate window captured by the selected video cameras are analyzed in block 406 by examining each pixel to determine whether the intensity of the pixel is above or below another prescribed threshold. If the intensity is below the prescribed threshold, then the corresponding pixel is designated as "black." Alternatively, if the intensity is above the prescribed threshold, then the corresponding pixel is designated as "white." By summing both the number of "white" pixels and the number of "black" pixels, and then calculating a percentage of either white pixels or black pixels over the area of a particular conductive pad encompassed by the appropriate window, an indication of the solder brick's coverage of the particular conductive pad can be obtained.

Printed circuit board 208 is also preferably inspected for solder bridges. As mentioned above, solder paste tends to be very specular. In contrast, a surface of printed circuit board 208 is typically very diffuse and therefore does not easily reflect light toward the selected video cameras. Accordingly, the images of a window encompassing a potential bridging site, which are captured by the selected video cameras, are analyzed in block 406 by examining the horizontal or vertical continuity of the reflected light detected by the selected video cameras. As a result, an indication of solder paste bridging across the potential bridging site can be obtained.

Solder bricks are also preferably inspected for irregularities that might be caused by voids, pin holes, or blow holes. This is done by creating "topographical maps" of the solder bricks and by examining the topographical maps to detect aberrations or secondary shapes as disclosed in U.S. Pat. No. 5,060,065.

It has been found that a hybrid approach to solder paste inspection, which combines both statistical process control and 100% inspection methods, is very useful for preventing both systematic and random defects occurring in the manufacture of printed circuit boards.

Having described one embodiment, numerous alternative embodiments or variations might be made. For example, it was described that the defect analyzer had only four video cameras disposed in an inspection head. However, this was merely an illustration. The defect analyzer according to the present invention might include more or fewer video cameras.

Also, the defect analyzer may be varied so that the inspection head is fixed and the printed circuit board under inspection is movable.

Also, it was described that solder bricks are inspected for improper height by projecting a pattern of light across each solder brick. However, this was also merely an illustration. Heights of solder bricks might also be inspected using laser ranging techniques.

Also, it was described that light triangulation techniques can be used for measuring heights of solder bricks. Light triangulation techniques might also be used for determining the overall flatness of a solder brick, and the perpendicularity of the sides of the solder brick.

Also, it was described that solder bricks are inspected for improper height by projecting a single "cross" pattern of light across each solder brick. However, this was merely an illustration. Multiple cross patterns of light might be projected across each solder brick, and the cross patterns might be continuously and successively scanned for creating a complete three dimensional profile of the solder brick.

Also, it was described that the dimensions of each viewing field are preferably 1 inch by 1 inch. However, this was also merely an illustration. Higher magnifications can be achieved by decreasing the size of the viewing fields. This might be necessary for obtaining more detailed inspections of the solder paste. For example, inspections according to the present invention might be performed using viewing fields having dimensions of 0.4 inch by 0.4 inch. With these dimensions, inspection head 102 would scan printed circuit board 208 at a slower rate of 0.4 inch/33 msec, or about 12 inches per second. This would result in a corresponding scanning rate of about 4.8 square inches per second, assuming a scan width of 0.4 inch.

Therefore, the invention should be limited only by the spirit and scope of the appended claims.

What is claimed is:

1. A method of inspecting solder bricks deposited on a printed circuit board, comprising the steps of:
   (a) sampling the solder bricks, thereby acquiring a plurality of solder brick samples;
   (b) projecting a pattern of light onto a top surface of each solder brick sample;
   (c) detecting reflected light associated with the top surface of each solder brick sample; and
   (d) analyzing the detected reflected light for determining if each solder brick sample has the proper height.

2. The method of inspecting solder bricks as recited in claim 1,
   wherein the projecting in step (b) includes projecting a portion of the pattern of light onto a surface of the printed circuit board near each solder brick sample, and
   wherein the detecting in step (c) includes detecting reflected light associated with the surface of the printed circuit board near each solder brick sample.

3. The method of inspecting solder bricks as recited in claim 1,
   wherein the pattern of light is a cross.

4. The method of inspecting solder bricks as recited in claim 3,
   wherein the analyzing in step (d) includes analyzing the detected reflected light using light triangulation techniques.

5. A method of inspecting a printed circuit board, and solder paste deposited on the printed circuit board during a solder paste deposition process, comprising the steps of:
   (a) inspecting the printed circuit board for random defects occurring in the solder paste deposition process, comprising the substep of
      (a1) inspecting all solder paste deposits to determine if each has been deposited on the printed circuit board; and
   (b) inspecting the printed circuit board for systematic defects occurring in the solder paste deposition process, comprising the substep of
      (b1) sampling the solder paste deposits to determine if each sample incorporates a solder brick having a proper height relative to a surface of the printed circuit board.

6. The method of inspecting a printed circuit board as recited in claim 5,
   wherein the inspecting in substep (a1) includes
      (i) directing light toward each solder paste deposit and a corresponding conductive pad on the surface of the printed circuit board, and
      (ii) detecting differences between reflected light levels associated with each solder paste deposit and reflected light levels associated with the corresponding conductive pad.

7. The method of inspecting a printed circuit board as recited in claim 5,
   wherein the inspecting in substep (b1) includes
      (i) projecting a pattern of light onto a top surface of each solder brick sample and onto a surface of the printed circuit board near each solder brick sample,
      (ii) detecting reflected light associated with the top surface of each solder brick sample and the surface of the printed circuit board near each solder brick sample, and
      (iii) analyzing the detected reflected light for determining if each solder brick sample has the proper height.

8. The method of inspecting a printed circuit board as recited in claim 7,
   wherein the pattern of light is a cross.

9. The method of inspecting a printed circuit board as recited in claim 8,
   wherein the detected reflected light is analyzed using light triangulation techniques.

10. The method of inspecting a printed circuit board as recited in claim 5,
    wherein the inspecting in step (a) further comprises the substep of
       (a2) inspecting all solder paste deposits to determine if each incorporates a solder brick giving proper coverage to a corresponding conductive pad on the surface of the printed circuit board.

11. The method of inspecting a printed circuit board as recited in claim 10, wherein the inspecting in substep (a2) includes
- (i) directing light toward each solder brick and the corresponding conductive pad for reflection to at least one video camera,
- (ii) capturing an image of each reflection using the at least one video camera,
- (iii) detecting an intensity of each pixel in each captured image relative to a prescribed threshold, and
- (iv) calculating a percentage of pixels in each captured image above or below the prescribed threshold, thereby obtaining an indication of each solder brick's coverage of the corresponding conductive pad.

12. The method of inspecting a printed circuit board as recited in claim 10, wherein the inspecting in step (a) further comprises the substep of
- (a3) inspecting all solder paste deposits to determine if each incorporates a properly shaped solder brick.

13. The method of inspecting a printed circuit board as recited in claim 12, wherein the inspecting in step (a) further comprises the substep of
- (a4) inspecting the printed circuit board to determine if solder bridges exist between adjacent conductive pads on the surface of the printed circuit board.

14. The method of inspecting a printed circuit board as recited in claim 13, wherein the inspecting in substep (a4) includes
- (i) directing light toward each portion of the surface of the printed circuit board between the adjacent conductive pads, and
- (ii) detecting reflected light associated with each portion of the surface between the adjacent conductive pads, thereby determining if the reflected light is continuous between the adjacent conductive pads.

* * * * *